United States Patent [19]

Nestler et al.

[11] Patent Number: 4,641,973
[45] Date of Patent: Feb. 10, 1987

[54] METHOD AND APPARATUS FOR MEASUREMENT OF THE CONCENTRATION OF A COMPONENT OF A MIXTURE

[75] Inventors: Volker Nestler, Hamburg; Wolfgang Olsowski, Norderstedt, both of Fed. Rep. of Germany

[73] Assignee: H. Maihak AG, Hamburg, Fed. Rep. of Germany

[21] Appl. No.: 420,613

[22] Filed: Sep. 20, 1982

[30] Foreign Application Priority Data

Sep. 22, 1981 [DE] Fed. Rep. of Germany ....... 3137658

[51] Int. Cl.$^4$ .............................................. G01J 3/51
[52] U.S. Cl. .................................. 356/418; 250/343; 250/351; 356/51
[58] Field of Search ................ 356/51, 418; 250/343, 250/351

[56] References Cited

U.S. PATENT DOCUMENTS

| | | | |
|---|---|---|---|
| 3,023,661 | 3/1962 | McClusky et al. | 356/51 |
| 3,279,308 | 10/1966 | Bartz et al. | 356/51 |
| 3,706,497 | 12/1972 | Lindberg | 356/418 |
| 3,735,127 | 5/1973 | Astheimer | 250/346 |
| 3,860,818 | 1/1975 | Stalder et al. | 356/51 |
| 3,878,107 | 4/1975 | Pembrook et al. | |
| 3,968,367 | 7/1976 | Berg | 250/339 |
| 3,994,592 | 11/1976 | Lardon et al. | 356/408 |
| 4,076,424 | 2/1978 | Ida | 356/434 |
| 4,087,690 | 5/1978 | Prober | 356/51 |
| 4,090,792 | 5/1978 | Bunge . | |
| 4,205,913 | 6/1980 | Ehrfeld et al. | 356/51 |
| 4,421,411 | 12/1983 | Ida | 356/418 |

FOREIGN PATENT DOCUMENTS

| | | |
|---|---|---|
| 0032852 | 7/1981 | European Pat. Off. . |
| 2364775 | 7/1974 | Fed. Rep. of Germany . |
| 2530480 | 1/1977 | Fed. Rep. of Germany . |
| 2643331 | 3/1978 | Fed. Rep. of Germany . |
| 2727976 | 1/1979 | Fed. Rep. of Germany . |
| 3021041 | 6/1980 | Fed. Rep. of Germany . |

*Primary Examiner*—F. L. Evans
*Assistant Examiner*—Joel L. Harringa
*Attorney, Agent, or Firm*—Roylance, Abrams, Berdo & Goodman

[57] ABSTRACT

A method and apparatus for measuring the concentration of a substance capable of absorbing infrared, visible or ultraviolet radiation energy, the substance being in a mixture. The method and apparatus involve passing a beam of radiant energy having predetermined spectral response characteristics through the mixture, modulating the beam at a predetermined frequency $\omega$ to form two sequential separate intervals of radiation, the two intervals being separated from each other by dark intervals and being different from each other in spectral response, controlling the first one of the radiation intervals with a filter which selectively absorbs or transmits energy in the spectral region of the absorption of the substance being measured, controlling the second one of the radiation intervals with a filter which does not selectively absorb or transmit energy in the spectral region of the absorption of the substance being measured or in the spectral region of interference components, measuring the intensities of the radiation intervals after the beam has passed through the mixture using a wide-band detector to produce two output signals, phase rectifying the detector output signals with the frequencies $\omega$ and $2\omega$ to form two signals $S_\omega$ and $S_{2\omega}$ and forming the ratio of the two signals as a measure of the concentration of the components of interest.

7 Claims, 10 Drawing Figures

METHOD AND APPARATUS FOR MEASUREMENT OF THE CONCENTRATION OF A COMPONENT OF A MIXTURE

SPECIFICATION

This invention relates to a method and apparatus for measuring the concentration of a gas in a gas matrix which is capable of absorbing radiant energy in various spectral regions, or of a substance dissolved in a solvent.

BACKGROUND OF THE INVENTION

With the use of nondispersive gas concentration measuring devices, i.e., gas analyzers which operate on optical principles, and which contain neither gratings nor prisms, the measured value is customarily obtained from the comparison of two light fluxes, i.e., one light flux or beam which is strongly influenced by the measured object and one light flux or beam which is influenced very little, or not at all, by the substance being measured.

Processes and devices are known for this type of concentration measurement wherein the light beams simultaneously pass through optical paths which are geometrically separated from each other, or, wherein both light beams pass through the same optical path in succession.

In the second process mentioned above, it is possible to use two filter cells filled with different gases or dissolved substances or two interference filters, of which the center wavelengths differ from each other, wherein the filter cells or the interference filters are periodically and serially inserted in the beam path. The filter functions are thereby so selected that only one of the two light beams at a time, in sequence, can be influenced by the substance being measured. Measuring devices in accordance with the second process mentioned above are when using gases or dissolved substances as a filter, (this being referred to as negative selective modulation) gas filter correlation photometers, and when using interference filters (positive selective modulation) interference filter correlation photometers. Either correlation or bifrequency photometers can be used in conjunction with the same electronic analysis device.

A correlation photometer is shown in the *Review of Scientific Instruments*, Vol 49, page 1520 (1978), in which the ratio $(I_M-I_R)/I_R$ is used as the measure of the concentration of the measured substance in the optical beam path, wherein $I_M$ and $I_R$ indicate the intensities of the measured and reference signals, respectively. The differential signal $(I_M-I_R)$ is, thus, obtained by phase-sensitive modulation of the detector signals having the frequency $\omega$, wherein $\omega$ is the modulation cycle frequency.

To determine $I_R$, the light intensity during the reference signal phase is also mechanically modulated with the frequency $\omega'$, which is far higher than $\omega$ and the detector signal is modulated with the frequency $\omega'$ in respect to the phase. Thereafter the ratio is formed.

BRIEF DESCRIPTION OF THE INVENTION

An object of the invention is to provide a method and apparatus which permits gas concentration analysis based on the use of a correlation or bifrequency photometer which can be produced at somewhat lower cost and which provides improved linearity of the measured values at the input to a linearization circuit.

A further object is to provide a method and apparatus wherein higher concentrations can be measured more precisely.

Briefly described, the invention includes a method for the measurement of the concentration of a substance capable of absorbing infrared, visible or ultraviolet radiation energy, the substance being in a mixture, comprising passing a beam of radiant energy having predetermined spectral response characteristics through the mixture; modulating the beam at a predetermined frequency to form two sequential separate intervals of radiation, the two intervals being separated from each other by dark intervals and being different from each other in spectral response; controlling the first one of the radiation intervals with a filter which selectively absorbs or transmits energy in the spectral region of the absorption of the substance being measured, controlling the second one of the radiation intervals with a filter which does not selectively absorb or transmit energy in the region of the absorption of said substance or in the region of spectra of interference components; measuring the intensities of the radiation intervals after the beam has passed through the mixture using a wide-band detector to produce two output signals; phase rectifying the detector output signals with the frequencies $\omega$ and $2\omega$ to form two signals $S_\omega$ and $S_{2\omega}$; and forming the ratio of the two signals as a measure of the concentration of the components of interest.

As will be recognized, in accordance with the invention, nondispersive single beam photometry is used with a gas filter or interference filter carousel as modulator. With modulation of the measured beam two different spectral distribution functions in timed succession one after the other, which are separated from each other by dark intervals, are obtained. The measured beam undergoes a specific spectral absorption for the measured substance by passage through the measuring region. The beam which is so modulated then impacts on a detector, the output signal of which is subjected to electronic Fourier analysis. The ratio of the first and second Fourier coefficients represents the value of concentration of the optically absorbing substance. The solution according to the invention is simpler than two-beam photometry, in respect to the construction and the adjustment, and can therefore be used for "in situ" measurement wherein the gas being measured is not confined in a test chamber, and is unresponsive to changes in the beam path which can occur as a result of window contamination.

BRIEF DESCRIPTION OF THE DRAWINGS

In order that the manner in which the foregoing and other objects are obtained and as that the invention can be understood in detail, particularly advantageous embodiments thereof will be described with reference to the accompanying drawing, which form a part of this specification, and wherein.

DETAILED DESCRIPTION OF THE DRAWINGS

Figure 1:
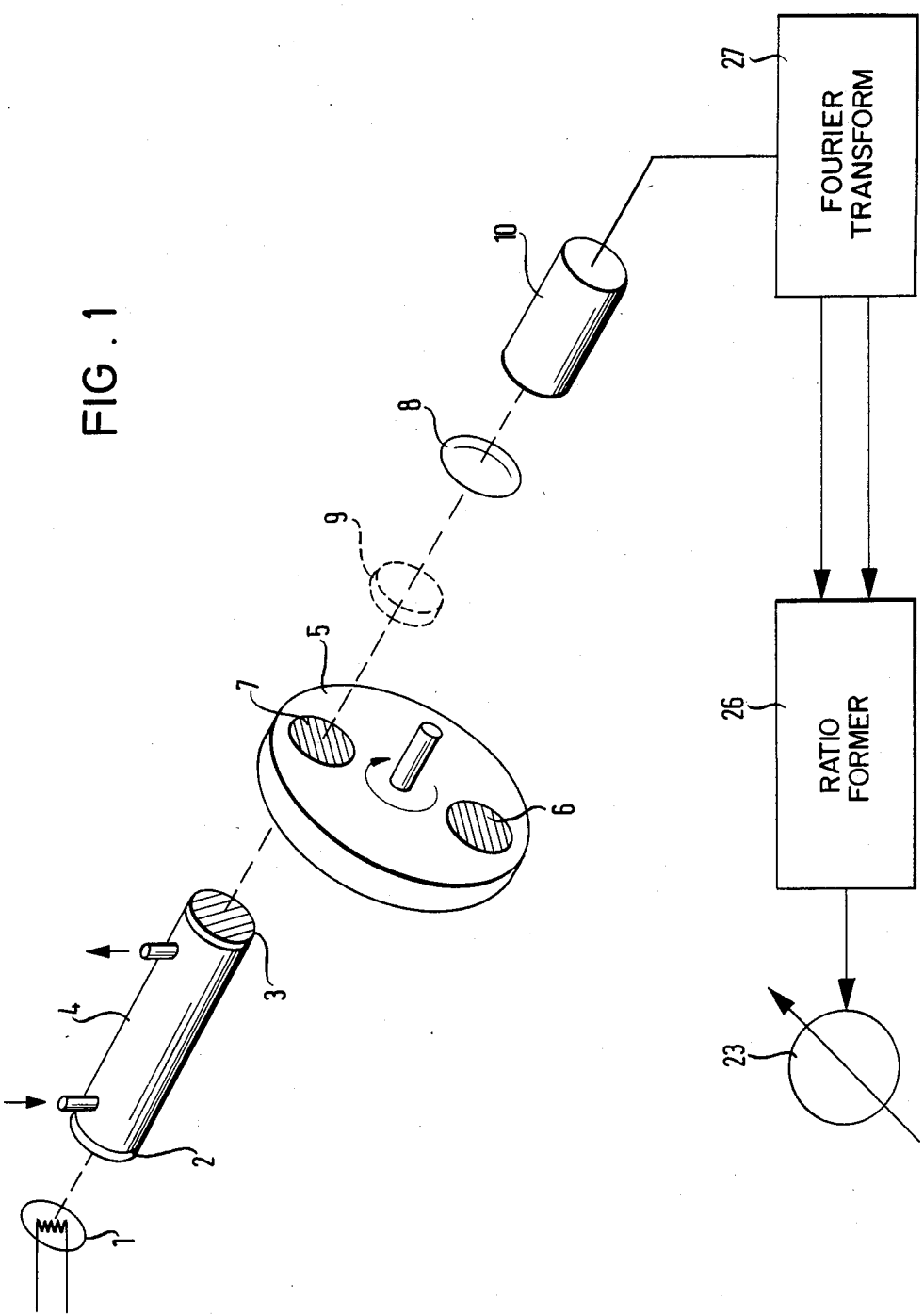
FIG. 1 is a simplified schematic perspective view of a measuring apparatus incorporating the principles of the present invention.

Referring to the drawings in detail, a single beam photometer such as that illustrated in FIG. 1 has, as part of its basic construction, a source of radiation 1 which can be, for example, a thermal emitter producing radiation in the infrared range. Emitter 1 produce a beam which passes through a measuring chamber 4 with the substance to be measured contained therein. The chamber is sealed to separate it from its surroundings by windows 2 and 3, the windows being transparent to radiation in the spectral region of interest to permit penetration of the beam through the substance to be measured. Measuring chamber 4 can, for example, consist of a closed chamber such as a cell. Alternatively, it can be a processing chamber into which and out of which gas is continually passing for an "in situ" measuring process, as indicated by the arrows.

In measuring chamber 4, the spectral distribution of the light intensity undergoes a characterisitic change as a function of the concentration of the substance being measured. After the beam emerges from window 3 of chamber 4, it is modulated by a diaphragm wheel 5 which rotates so any one point on the wheel has a periodic frequency $\omega$ with respect to the beam, modulating the beam both in intensity and also spectrally, i.e., as to wavelength or frequency. The manner in which diaphragm wheel 5 operates as a modulator will be described in greater detail hereinafter.

After the beam is modulated, it is focused by a lens 8 on to detector 10 which, for example, can be a pyroelectric receiver, or a semiconductor detector responsive to radiation in the infrared and nondispersive infrared regions. Diaphragm wheel 5 carries filters 6 and 7 which are sequentially moved into the path of the beam. If filters 6 and 7 are gas filters, an additional stationary interference filter 9 is provided in the beam path. The modulator diaphragm wheel 5 can also be arranged between emitter 1 and measuring chamber 4, or even in measuring chamber 4 itself. The apparatus can also include the remaining components shown in FIG. 1, i.e., a Fourier analyzer 27, a divider or ratio former 26, and a display device 23.

Figure 2:
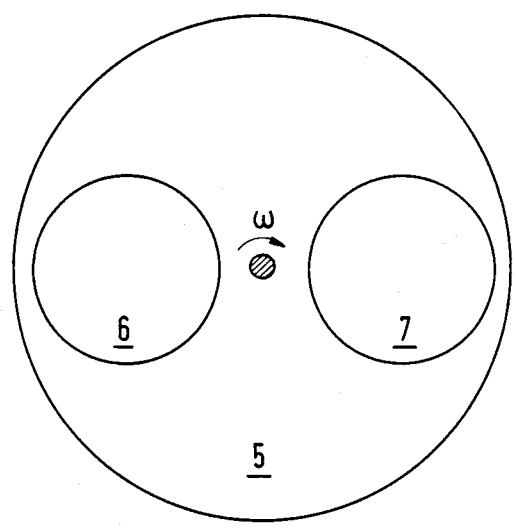
FIG. 2 is a plan view of a diaphragm disc modulator usable in the apparatus of FIG. 1.

The diagram of FIG. 2 shows, in plan view, an example of a modulator diaphragm wheel 5 usable in the apparatus of FIG. 1 which includes two interference filters 6,7, which are each moved with a cyclic frequency $\omega$—in respect to the wheel 5—into and out of the beam path so that the beam is modulated with two filters with the cycle frequency $2\omega$. That is, the wheel 5 rotates at a speed so that if the wheel 5 carried one filter the beam would be modulated at a frequency of $\omega$ and if it carried two filters being in opposition the beam is modulated at a frequency $2\omega$. The transmission peak of filter 6 is selected to be at the wave length $\lambda_A$ at which the component A, the concentration of which is to be measured, has its absorption band. If interference filter 6 is moved as the first filter into the beam path, then the interference filter 7 having a center wave length $\lambda_O$ which does not lie in the region of the absorption band of component A, follows.

Altogether, the beam from source 1 therefore undergoes spectral and intensity modulation, as shown in the diagrams of FIGS. 3A to 3E.

Figure 3A:
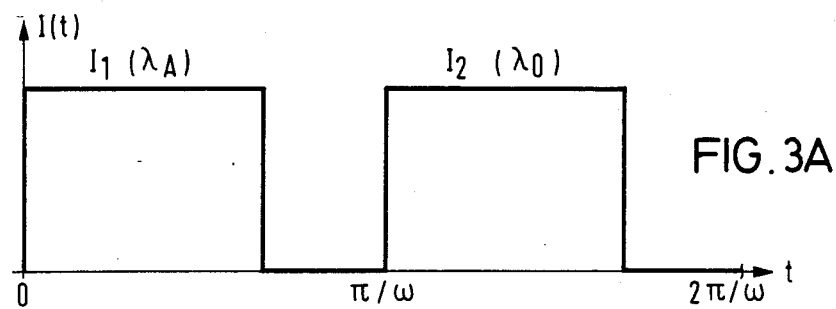
FIGS. 3A–E are diagrams showing periodic changes in intensity and transmission characteristics of the apparatus as a function of modulation frequency.
Figure 3B:
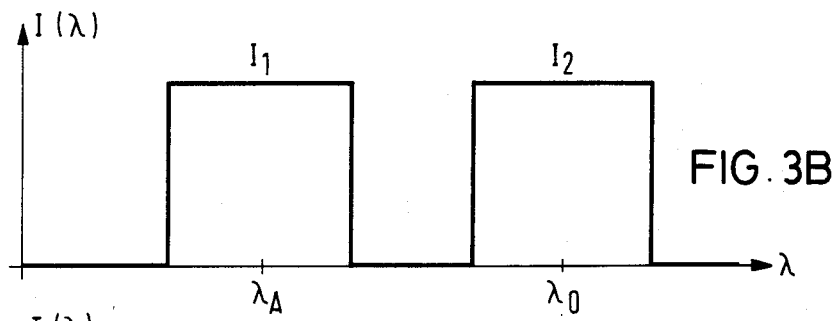

FIG. 3A shows the periodic change of the light intensity, without the presence of any component being measured, whereupon no radiation absorption occurs. FIG. 3B is a diagram of the corresponding spectral distribution of the intensities $I_1$ and $I_2$.

Figure 3C:
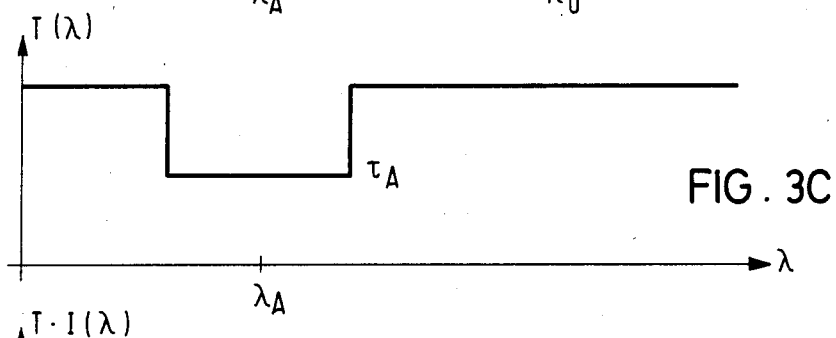
Figure 3D:
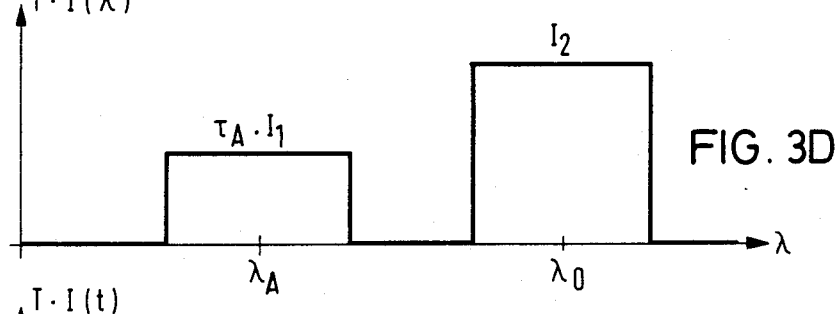
Figure 3E:
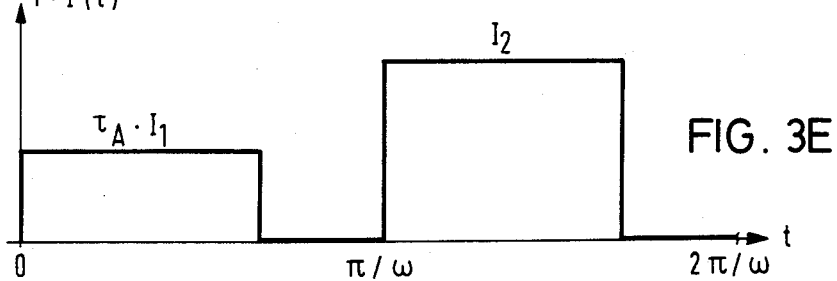

The absorption by the measured component A produces a change or defect in the transmission ($\tau_A < 1$) of the measured area at a specific spectral point $\lambda_A$ (FIG. 3C). This leads to a reduction of the light intensity $I_1$ at $\lambda_A$, while the light intensity $I_2$ remains the same. This is shown in FIG. 3D. In FIG. 3E, the effect of the measured component A is shown on the time sequence of the light intensity. The measured effect therefore resides in the difference between the signals 3A and 3E.

Figure 4:
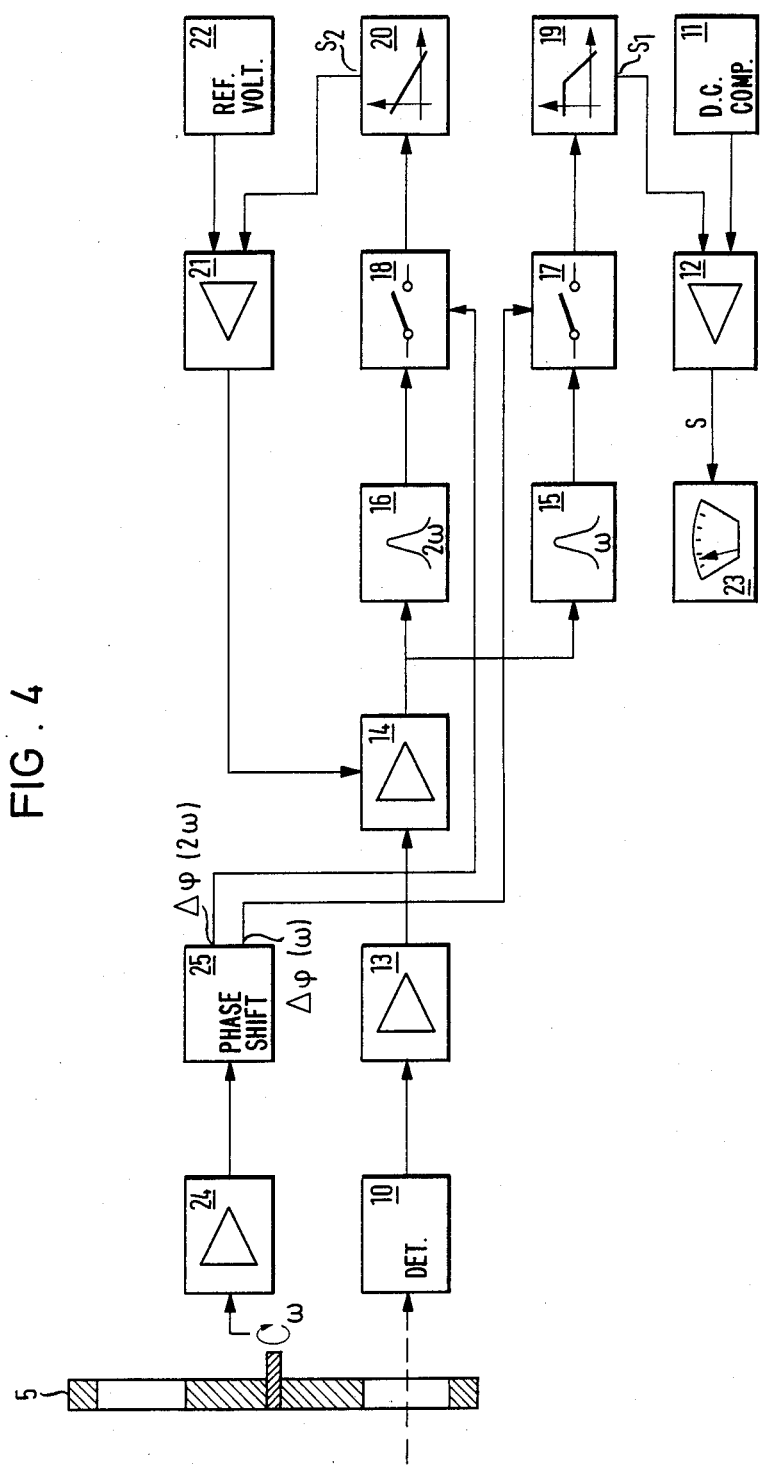
FIG. 4 is a schematic block diagram of electronic apparatus usable with the apparatus of FIG. 1 for the purpose of processing the data to arrive at measured values.

The output signals of detector 10 are processed by evaluation by means of measured value processing electronics which include a two channel, lock-in amplifier, of which the operation can be seen by reference to the block diagram of FIG. 4. The intensity of the light from source 1 modulated by modulator diaphragm wheel 5 with periodic frequency $\omega$ is converted in detector 10 into an electrical signal, which is first amplified by the preamplifier 13 and then further amplified by an adjustable amplifier 14. The detector signal which is thus treated is then separated into two portions of its frequency spectrum (Fourier analysis).

In a first measurement channel, the signal portion with the frequency $\omega$ is extracted by a selective filter 15 and is rectified in phase-synchronization to $\omega$ by a phase sensitive detector 17 which is series connected. The resulting signal is then smoothed by a low pass filter 19, producing a smoothed signal $S_1$ from the first channel.

The process is similar in the second channel. A filter 16 selects the signal portion with the frequency $2\omega$ which is rectified in phase synchronization to $2\omega$ by a phase sensitive detector 18. The control signals for $\omega$ and $2\omega$ are produced by a reference signal amplifier 24 and a phase shifter 25. The signal in the second channel is then filtered by an integrator 20 and is passed to a variable amplifier 21 which compares the signal $S_2$ with a reference voltage from a reference voltage generator 22 and produces a signal which controls the gain of adjustable amplifier 14. Thus, it is guaranteed that signal $S_1$ of the first channel which is smoothed by low pass filter 19 and amplified by means of amplifier 12, and is then delivered to display device 23, is proportional to the ratio of the first and second Fourier coefficients of the signal mixture from FIGS. 3A and 3E. A direct voltage from a direct voltage source 11 can be superposed on signal $S_1$ for compensation purposes. Analysis of the periodic signal yields the first and second Fourier coefficients $F_1$ and $F_2$, with the assumption that the geometric shapes of the filter holders of modulator diaphragm wheel 5 are exactly the same.

$$F_1 = a_1(\tau_A I_1 - I_2) \quad (1)$$

$$F_2 = a_2(\tau_A I_1 + I_2) \quad (2)$$

In these expressions, $a_1$ and $a_2$ are instrument constants which are determined by the geometric arrangement.

With the assumption that the separate filters 6 and 7 are such that their total transmissions are equal, and such that $I_1$ equals $I_2$, the following expressions represent the Fourier coefficients:

$$F_1 = a_1(\tau_A - 1)I_1 \quad (3)$$

$$F_2 = a_2(\tau_A + 1)I_2 \quad (4)$$

The measure signal generated for display is the ratio of these two quantities, which simplifies to:

$$S_1 \sim (1-\tau_A)/(1+\tau_A) \quad (5)$$

By the ratio formation, the signal is made independent of the light intensity and, thus, is drift free with respect to "gray", and therefore spectrally independent intensity variations such as might arise, for example, from window contamination.

The transmission factor $\tau_A$ of the measured substance A is an integral function of the spectral transmission, averaged from the interference filter transmission curve at $\lambda_A$.

For small products $\epsilon(\lambda) cL$, where $\epsilon(\lambda)$ is the specific absorption coefficient averaged in the transmission range of the interference filter, c is the concentration of the measured component A, and L is the optical path length in the measured medium, then the transmission can be represented by a Taylor series $$\tau = 1 - \epsilon \cdot cL^\pm \ldots \quad (6)$$

This approximation can always be adjusted by a suitable selection of the spectral transmission of the window of the interference filter as well as the optical path length L of measuring chamber 4, configured, if possible, as a cell. If the approximation as in equation 6 is used in equation 5, then, $$S_1 \sim (\epsilon \cdot cL)/(2+\epsilon cL) \approx \tfrac{1}{2}(\epsilon \cdot cL) \quad (7)$$

The signal is a strongly monotonic expanding function of the concentration of the measured component A. The sensitivity of the process according to the invention is essentially determined by the actual optical measurement area 1 and by the spectroscopic data of the measured component A, i.e., by $\epsilon(\lambda)$, and depends, with the bifrequency process, upon the selection of the central wave length and the half peak transmission band width (HWB) of the interference filter, and with the gas filter correlation process, upon the concentration of the correlation gas in the filter cell.

In practice, a compromise must be made between the responsiveness or sensitivity and the linearity, whereby the linearity is not to be regarded as being critical. According to expression 5 above, the signal $S_1$ also includes the measured component transmission in the denominator of the ratio. By this, the sensitivity with smaller concentrations is somewhat reduced, but at the same time for non-linearity of the transmission at higher concentrations, is compensated.

It is not to be expected that both interference filters 6 and 7 of modulation wheel 5 have the same total transmission because they are subject to deviations of the position of the transmission peak and of the width at half peak transmission band width for example due to manufacturing tolerances. Therefore, one must recognize that source 1 and detector 10 have spectral paths which influence the total transmission in both channels. Such differences $(I_1-I_2)$ however, cause some problems with the apparatus adjustment. Particularly, the signal $S_1$ is not zero when the concentration is at zero. This is valid for gas filter correlation technology, wherein intensities $I_1$ and $I_2$ are different from the outset by the selective preabsorption in the gas filter.

Two steps are suggested for compensation of these effects. For one, a mechanical device can be provided which acts as adjustable diaphragm for the gas filter or interference filter which carries the higher total transmission. This diaphragm is mounted on the rotating modulating diaphragm wheel and covers the beam opening of the filter so that the compensation $(I_1 = I_2)$ occurs without the presence of measured component A.

Adjustment by means of an electronic device is much simpler if a constant direct voltage $U_O$ is fed to signal $S_1$ (elements 11 and 12 of FIG. 4) to allow the signal to go to zero whenever the concentration of the measured component is zero.

$$S = U_o + b(I_2 - \tau_A I_1)/(I_2 + \tau_A I_1) \quad (8)$$

In this equation, b is a constant. The adjustment at $c=0 => \tau_A = 1$ is now shown as, $$U_o = -b(I_2 - I_1)/(I_2 + I_1) \quad (9)$$

at this point. If the appearance of interference components in the measuring chamber is to be expected, such that the absorption bands overlap with those of the measured component, then compensation measures for that are also possible. With the bifrequency process, the spectral position $\lambda_O$ of the reference interference filter is selected such that it includes another part of the interference component bands, i.e. that part where the measured component A itself does not absorb or absorbs only slightly. Then the reduction of intensity at $\lambda_A$ by the interference component is compensated by means of a proportional reduction at $\lambda_O$.

If a gas filter is used, both correlation cells can additionally be filled with the interference component, so that the influence of that component is eliminated in measuring chamber 4. Of course, the customary filter technology can also be used, for example, with filter cells installed in stationary positions in the beam path filled with the interference components.

Figure 5A:
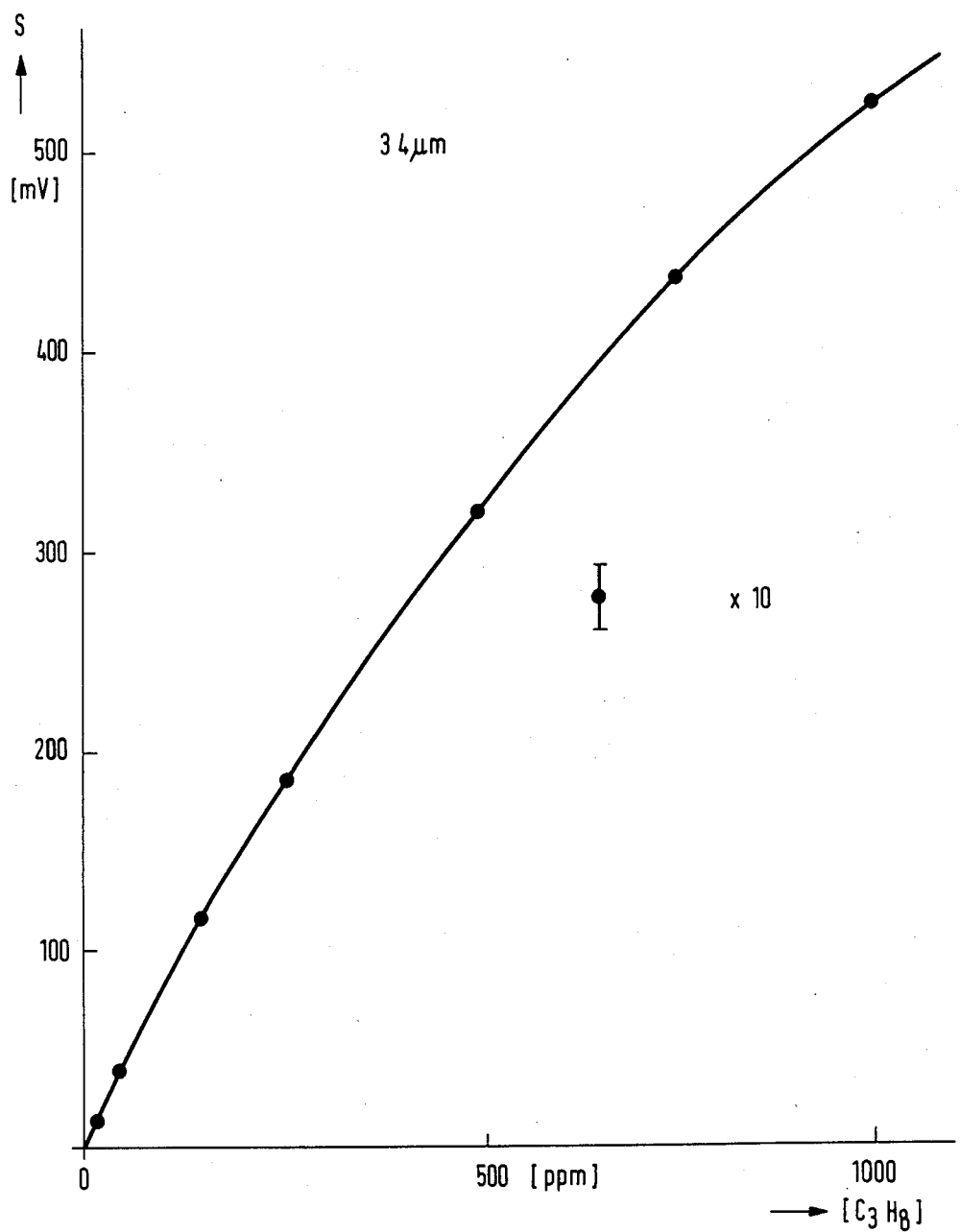
FIGS. 5A and 5B are graphs showing measured results for examples of use of the gas analysis techniques in accordance with the present invention.

FIG. 5A shows a first exemplary use of the gas analysis, i.e., the measurement resulting from a propane measuring device. Herein, it was processed with gas filter correlation wherein the cells were filled 100% with nitrogen or $C_3H_6$. The cells were 150 cm long, and the spectral area was 3.4 μm, filtered through a narrow band interference filter.

Figure 5B:
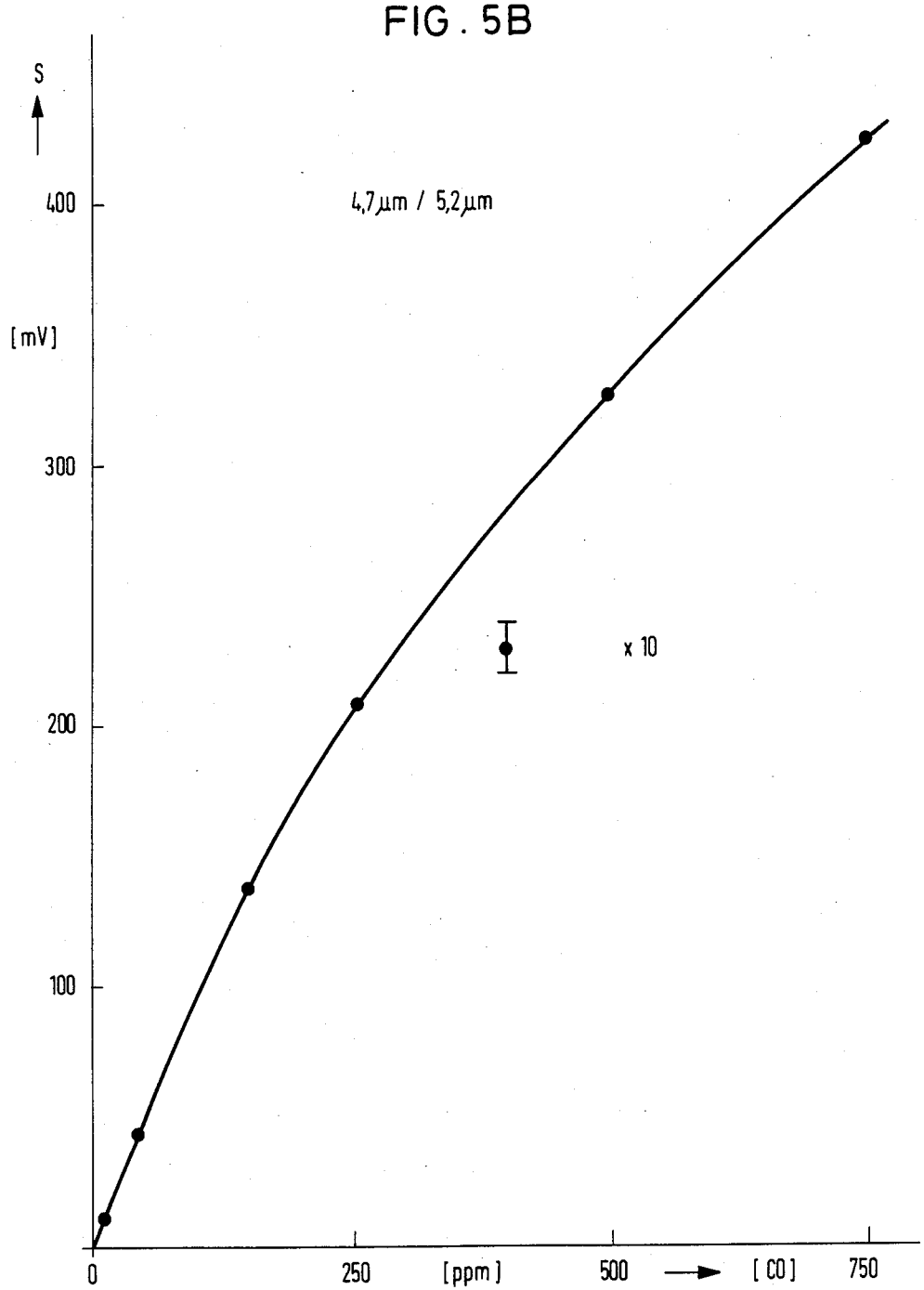

FIG. 5B shows the resulting measurement from the second example of the use of the technique wherein the measurement results were obtained using the bifrequency process wherein $\lambda_A = 4.63$ μm, $HWB_A = 0.17$ μm, $\lambda_O = 5.24$ μm and $HWB_O = 0.08$ μm. A cell of L=150 cm was used. In both cases a pyroelectric detector was used. While certain advantageous embodiments have been chosen to illustrate the invention it will be understood by those skilled in the art that various changes and modifications can be made therein without departing from the scope of the invention as defined in the appended claims.

What is claimed is:

1. An apparatus for the measurement of the concentration of a substance capable of absorbing infrared, visible or ultraviolet radiation energy, the substance being in a mixture, comprising:

source means for generating a beam of radiant energy having predetermined spectral response characteristics;

chamber means for containing the mixture, said chamber means having windows transparent to the beam of radiant energy aligned with each other and said beam;

means serially connected in an optical path with said source means and said chamber means for modulating the beam at a predetermined frequency to form two sequential separate intervals of radiation, said means for modulating including a first filter for controlling the first one of the radiation intervals which first filter does one of selectively absorbing and transmitting energy in the spectral region of the absorption of the substance being measured, and a second filter for controlling the second one of the radiation intervals which second filter does not selectively absorb and does not selectively transmit energy in the spectral region of the absorption of the substance being measured and in the spectral region of interference components, and said means for modulating including means to create dark intervals between said first and second filters;

a wide-band detector at the end of said optical path for measuring the intensities of the radiation intervals after the beam has passed through the mixture to produce an output signal;

a series connected lens for focusing the radiant energy of the beam on said detector; and circuit means connected to the output of said detector forming a signal representative of the concentration of the substance and for displaying the signal thus formed, said circuit means including phase shifter circuit means coupled to said means for modulating for producing reference output signals, amplifier means including a first variable gain amplifier for amplifying the output signal from said detector, first and second frequency selective filters connected to receive the output of said amplifier means and for passing portions thereof at selected frequencies, first and second phase rectifier means connected to receive the outputs of said phase shifter circuit means and the outputs of said first and second frequency selective filters for rectifying said outputs, a low-pass filter connected to receive the rectified signal from said first rectifier means, a first voltage reference source, a display amplifier having inputs connected to receive the outputs of said low-pass filter and said first voltage reference source, display means for displaying the output of said display amplifier, a second voltage reference source, an integrator circuit connected to receive the output of said second rectifier means, and a second variable gain amplifier having inputs connected to receive the outputs of said integrator circuit and said second voltage reference source and an output connected to control the gain of said first variable gain amplifier.

2. An apparatus according to claim 1, wherein said first filter is a gas filter selected to absorb radiation at a wavelength characteristically absorbed by said substance.

3. An apparatus according to claim 1, wherein said first filter is an interference filter selected to transmit radiation at a wavelength characteristically absorbed by said substance.

4. An apparatus according to claim 1, wherein said second filter in a gas filter which selectively absorbs or transmits no wavelength characteristically absorbed by the measured substance in the mixture or by its interference spectra.

5. An apparatus according to claim 1 wherein said second filter is an interference filter which selectively transmits no wavelength in the range of the absorption spectrum of the substance being measured nor of its interference spectra.

6. An apparatus according to claim 1 wherein said means for modulating modulates the beam at two predetermined frequencies $\omega$ and $2\omega$.

7. An apparatus according to claim 6 wherein said circuit means phase rectifies the output signal of said wide band detector with the frequencies $\omega$ and $2\omega$ to form signals $S_\omega$ and $S_{2\omega}$ and forms the ratio of the two signals as a measure of the concentration.

* * * * *